United States Patent [19]
Seawright et al.

[11] Patent Number: 6,057,366
[45] Date of Patent: May 2, 2000

[54] METHOD OF TREATMENT OF CANCER AS WELL AS METHOD OF INHIBITION OF LACTATION IN MAMMALS

[75] Inventors: Alan Andrew Seawright, Upper Brookfield; Peter Brenchley Oelrichs, St. Lucia; Jack Chakmeng Ng, Wishart; John Keith MacLeod, Weetangera; Annemarie Ward, Palmerston, all of Australia; Lothar Schaeffeler, Bonn-Bevel, Germany; Raymond Maurice Carman, Chapel Hill, Australia

[73] Assignees: The University of Queensland; The Australian National University, both of Australia

[21] Appl. No.: 08/700,447
[22] PCT Filed: Feb. 28, 1995
[86] PCT No.: PCT/AU95/00097
§ 371 Date: Mar. 4, 1997
§ 102(e) Date: Mar. 4, 1997
[87] PCT Pub. No.: WO95/22969
PCT Pub. Date: Aug. 31, 1995

[30] Foreign Application Priority Data

Feb. 28, 1994 [AU] Australia ................................. PM4109
Apr. 20, 1994 [AU] Australia ................................. PM5205

[51] Int. Cl.[7] ........................... A61K 31/22; A61K 31/12
[52] U.S. Cl. ........................................... 514/546; 514/675
[58] Field of Search ...................... 514/675, 546

[56] References Cited

PUBLICATIONS

Chang, C et al.; "Isolation and Structure Elucidation of Growth Inhibitors for Silkworm Larvae from Avocado Leaves" *Agr Biol Chem*, 39(5), 1975, pp. 1167–1168.
Prusky, D et al.; "Possible Involvement of an Antifungal Diene in the Latency of Colletotrichum gloeosporioides on Unripe Avocado Fruits"; *Phytophathology*, 72(12), 1982, pp. 1578–1582.
Bull, Steven D et al.; "Synthesis of the Avocado Antigungal, (z,Z)–2–Hydroxy–4–oxohenicasa–12, 15–dien–1–yl Acetate", *Aust J Chem.* 47, 1994; pp. 1661–1672.
Craigmill, Arthur L, et al, et al.; "The Toxicity of Avocado (*Persea americana*) Leaves for the Lactating Mammary Gland of the Goat"; *Poisonous plants*: Proceedings of the third international Symposium; 1st Edition Iowa State Univeristy Press; 1992; pp. 623–625.
Craigmill, Arthur L, et al.; "Toxicity of Avocado (*Persea Americana* (Guatamalan var) Leaves: Review and Preliminary Report"; *Vet Hum Toxicol* 26(5) Oct. 1984; pp. 381–383.
"The Toxicity of Avocado (*Persea Americana*) Leaves for the Lactating Mammary Gland of the Goat" at the Proceedings of the Third International Symposium of Poisonous Plants, 1989, 623–625.
"The Toxicity of Avocado Leaves for the Heart and Lactating Mammary Gland in the Mouse" by Sani, et al. presented at the 4th International Symposium on Poisonous Plants in 1993.
Brown, Brian I., 1972, J. Agric. Food Chem. 20 753–757.
Prusky, et al., 1983, Physiological Plant Pathology 22 189–198.
Prusky, et al., 1985, Physiological Plant Pathology 27 267–279.
Prusky, Dov, 1988, Plant Disease 72(5) 381–384.
Prusky, et al., J. Phytophathology 123 (2) 140–146.
Karni, et al., 1989, Physiological and Molecular Plant pathology 35 367–374.
Sivanathan, et al.,1989, J. Phytopathology 125(5) 97–109.
Prusky, et al., 1990, Physiological and Molecular Plant Pathology 37 425–435.
Prusky, et al., 1991, Physiololgical and Molecular Plant Pathology 39 325–334.
Plumbley, et al., 1993, Plant Pathology 42 116–120.
Prusky, et al., 1991, Plant Pathology 40 45–52.
Prusky, et al., 1991, Phytopathology 131(4) 319–327.

*Primary Examiner*—Jerome D. Goldberg
*Attorney, Agent, or Firm*—Knobbe, Martens, Olson & Bear, LLP

[57] ABSTRACT

A method of treating breast or ovarian cancer is disclosed by administering an effective amount of a compound obtained from an avocado plant.

17 Claims, 11 Drawing Sheets

(1)

(2)

METHOD OF TREATMENT OF CANCER AS WELL AS METHOD OF INHIBITION OF LACTATION IN MAMMALS This application is a 371 of PCT/AU95/00097, filed Feb. 28, 1995.

FIELD OF THE INVENTION

This invention relates to a method of treatment of cancer in mammals and in particular humans as well as a method of inhibition or prevention of lactation in mammals using compounds which may be obtained from avocado plants.

PRIOR ARTS

It is well known that avocado plant (ie *Persea americana*) leaves are toxic and this has recently been reported in Craigmill et al., Vet. Hum Toxicol 26 (5) October 1984 which demonstrated that the leaves of a Guatemalan variety avocado are toxic to dairy goats even after storage for two weeks at 4° C. This was also demonstrated in an article entitled "The Toxicity of Avocado (*Persea americana*) Leaves for the Lactating Mammary Gland of the Goat" at the Proceedings of the Third International Symposium of Poisonous Plants pp 623–625 (1989). Reference is made in the 4th International Symposium on Poisonous Plants in 1993 to a presentation by Sani et al., to a toxin obtained from avocado leaves which was responsible for demonstrated toxicity for the heat and lactating mammary gland of the mouse.

It has also been demonstrated that three long chain C17 aliphatic compounds (ie. 4-keto-2-hydroxy-1-acetate, a 1,2-dihydroxy-4 acetoxy compound and a 1,4-dihydroxy-2-acetoxy compound, each with a terminal acetylenic bond, which were isolated from immature avocado seed, flesh and skin appeared to be the main constituents of an unpleasant bitter type flavour. This has been reported in Brown, J Agr Food Chem 20 No 4 (1972) 753–757.

Reference is also made to the isolation of a compound 1-acetoxy-2-hydroxy-4-oxo-heneicosa-12,15-diene from avocado plants in the following references (i) Chang et al., Agr. Biol. Chem 39 (5) 1167–1168 (1975);
(ii) Prusky et al., Phytopathology Vol 72, No 12 1578–1582 (1982);
(iii) Prusky et al., Physiological Plant Pathology 22 189–198 (1983);
(iv) Prusky et al., Physiological Plant Pathology 27 269–279 (1985);
(v) Prusky Plant Disease Vol 72 No 5 381–384 (1988);
(vi) Prusky et al., J. Phytopathology 123 (2) 140–146 (1988);
(vii) Karni et al., Physiological and Molecular Plant Pathology (198) 35 367–374;
(viii) Sivanathan et al., J. Phytopathology 125 (2) 97–109 (1989);
(ix) Prusky et al., Physiological and Molecular Plant Pathology 37 425–435 (1990);
(x) Prusky et al., Physiological and Molecular Plant Pathology 39 325–334 (1991);
(xi) Prusky et al., Plant Pathology 40 45–52 (1991);
(xii) Prusky et al., J Phytopathology 132 (4) 319–327 (1991); and
(xiii) Plumbley et al., Plant Pathology 42 116–120 (1993).

The above compound from the reference (i) above was isolated from avocado leaves and inhibited the growth of silkworm larvae.

The remainder of the abovementioned references [ie. (ii) to (xiii)] are concerned with the above compound which when isolated from avocado fruit peel or whole fruits exhibits antifungal activity in relation to the fungus *Colletotrichum gloeosporioides* which infects avocado and causes anthracnose in ripe fruit. The levels of the compound in avocado fruit may be decreased by degradation of the compound which is catalysed by the enzyme avocado lipoxygenase. The activity of the enzyme may increase during ripening of the fruit owing to the decline of an inhibitor of the enzyme (ie. epicatechin). The above literature also shows that the above phenomena suggest that this is why infection by the fungus is latent in unripe fruit.

Surprisingly it has now been discovered that the compounds described herein in formula (1) herein have anti-cancer activity and that such activity is particularly relevant in regard to breast cancer or cancer which may effect the mammary gland.

It has also been surprisingly discovered that these compounds inhibit or prevent lactation in mammals.

SUMMARY OF THE INVENTION

It is therefore an object of the invention to provide a method of treatment of mammals suffering from cancer and in particular breast cancer as well as a method of inhibition or prevention of lactation in mammals by administering of the compounds of formula (1) herein to such mammals and in particular humans.

It is a further object of the invention to provide anti-cancer or anti-lactation compositions which may contain the above compounds.

In the above compounds of formulae (1) R may refer to a side chain of 4 to 20 carbons and more preferably 17 carbons which may tolerate a minor degree of unsaturation (e.g. (1, 2 or 3 unsaturated bonds) as well as a minor degree of branching. Preferred compounds have the formulae 1(*a*) and 1(*b*) as shown in FIG. 1.

The chemical Abstracts Index name of the active compound that was isolated from avocado leaves as discussed above is (+)-(Z,Z)-1-acetyloxy-2-hydroxy-12,15-heneicosadien-4-one. An alternative name which is used in the aforementioned prior art is cis,cis-1-acetoxy-2-hydroxy-4-oxoheneicosa-12,15 diene.

The naturally occurring compound is the (+) or R isomer. Both the (±) racemate and the (−) or S isomer have been synthesised. However, the S isomer does not fall within the scope of the invention.

The synthesis of the above compounds is described hereinafter.

The compound(s) utilised in the method of the invention may be utilised in any suitable relatively non toxic vehicle. The compound(s) are insoluble in water and thus the relevant compound utilized needs to be utilised with a suitable solvent such as a non toxic surfactant or detergent which may be dissolved in water in relatively low concentrations. An appropriate surfactant for use would be a nonionic solvent such as polyoxyethylene surfactants such as ethoxylates. Other surfactants include carboxylic amides, carboxylic acid esters or polyalkylene oxide block copolymers. Examples of specific surfactants include PEG esters of $C_2$–$C_{18}$ fatty acids, Tween 80 or polyethylene oxide sorbitan mono-oleate, Brij or polyoxyethylene alcohol. Triton-X or Polyethylene glycol p-isooctylphenyl ether, Triton-N or a range of polyoxyethylated alkyl phenols or Triton A-20 i.e. (4-1,1,3,3-tetra methylbutyl phenol polymer with formaldehyde and oxirane).

Other vehicles that may be used include Tris or 2-amino-2-hydroxymethyl-1,3-propanediol, DECON or Cremophor EL which also is a non ionic surfactant. The latter vehicle is used as a solubilizing factor in regard to insoluble active therapeutic agents.

It will also be appreciated that any suitable non toxic organic solvent could be utilised such as ethyl alcohol, propylene glycol or mixtures of ethyl alcohol and propylene glycol, dimethyl sulphoxide or dimethyl formamide. Oil emulsions such as INTRALIPID (ie. emulsified corn oil) may also be utilised.

The preferred mode of administration is orally where the compound may be administered in a suitable vehicle as described above.

Preferably the compound is administered up to 100 mg per kg of body weight of subject and more preferably up to 60 mg per kg of body weight of subject. Since avocado leaves are toxic concentrations higher than the above may be lethal to the subject. It is also preferred to administer the compound orally on a number of consecutive days at a concentration of 20–40 mg (more preferably 30 mg) per kg of body weight of subject.

The compound may also be administered in other conventional dosage forms as may be required inclusive of tablets or capsules. Use as an injectable has hitherto not been found so far to be as effective as an oral dosage form.

Preferably when using a liquid vehicle such as a surfactant it is preferred that the surfactant be diluted with water so that only a small proportion of the surfactant is contained in the liquid formulation which is administered to the subject. A suitable proportion of surfactant that may be used includes 0.5–10% and more preferably 0.5–1% of surfactant.

In relation to use of Tween 80, suitably a solution of 1% of Tween 80 in water is utilised. Concentrations of greater than 1% of Tween 80 may render the surfactant functioning as a purgative.

In relation to use of the compound as an anti-lactation agent, this may be carried out by injection (e.g. parenterally) of the compound at a dose of 30 mg/kg of subject using a suitable vehicle such as dimethyl sulphoxide or dimethyl formamide. Experiments of this kind have shown that after such administration the mammary gland was atrophic with few milk producing acini and extensive replacement of acini by adipose tissue.

It will also be appreciated that the above compound (z,z)-1-acetyloxy-2 hydroxy-12,15-heneicosadien-4-one may also be obtained from avocado leaves using the following steps:

(1) Chloroform extraction of milled freeze dried *Avocado americana* leaf, using continuous soxhlet extraction for 3 days.

(2) Evaporation of the extract under reduced pressure at 40° C. to dryness.

(3) The dried extract dissolved in n-hexane, added to a silica-gel column and eluted initially with n-hexane, followed by dichloromethane (DCM) and a gradient of ethyl acetate in DCM. Fractions from the column were collected and the active principled monitored by TLC and testing using lactating laboratory mice. Fractions containing the active principle were combined and dried under reduced pressure (40° C.).

(4) The dried sample from (3) was dissolved in n-hexane, added to a florisil column and eluted as in (3). Fractions containing the active principle were collected and dried as in (3).

(5) The dried sample from (4) was dissolved in a (methanol/water/chloroform/acetic acid) mixture and added to a XAD-2 reverse phase partition chromatography column. Elution with this solvent mixture resolved the active principle in a single band. This was concentrated to dryness using toluene to remove the last traces of acetic acid.

(6) The dried sample from (5) was dissolved in DCM and added to a silicic acid column. Elution with this solvent produced a pure active compound.

(7) The dried sample from (5) may also be purified by a preparative HLPC system using a silica column and eluting with up to 5% hexane in chloroform or DCM.

In relation to experimental demonstration of the anti cancer effect of the compound, such effect can be demonstrated from toxicology experiments whereby lethal doses of the compound may be investigated with respect to concentration, timing and route of administration. Subsequently xenografts may be established from human cell lines of breast and ovarian cancers.

Thereafter the therapeutic administration of the compound may be investigated to determine its anti cancer activity. This can be done in relation to the following sequence—

(a) Survival studies only initially;

(b) Post mortem analysis for tumor burden if required;

(c) Histological evaluation of tissues if required.

SYNTHESIS OF COMPOUNDS

This experimental protocol refers to the synthesis of the avocado antifungal, (Z,Z)-2-hydroxy-4-oxo-henicosa-12,15-dien-1-yl acetate (1a) hereinafter sometimes referred to as "persin", and thus confirms the structure of the compound as isolated from both avocado fruit and leaves, and provides the absolute configuration of the natural lipid.

In consideration of the structure (1a) and its possible biosynthesis, it is apparent that compound (1a) is extremely closely related structurally to the mono-glyceride (2a) of linoleic acid shown in FIG. 1A, even to the position and the (Z,Z)-stereochemistry of the two double bonds. Compound (1a) is the deoxa-derivative of glyceride (2a). The reaction (1a)–(2a), with insertion of an oxygen atom, could be carried out by a Baeyer-Villager type oxidation, but no enzymes or chemical procedures are known that will carry out the reverse process (2a)–(1a) with extrusion of one oxygen atom. Thus the biosynthesis of compound (1a) remains unknown.

However the considerable structural similarity between compounds (1a) and (2a) causes us to speculate that the biological activity of compound (1a) is due, at least in part, to the fact that this compound can mimic compound (2a), perhaps irreversibly, in glyceride syntheses. Thus compounds of the general type (1) (either with or without attached acetate groups) might be incorporated in place of monoglycerides (2) in glyceride biosyntheses. In this case, a general synthesis of compounds (1) with a variety of fatty side chains (R) would provide a range of compounds for biological screening, not just against anthracnose but in all screens involving lipid or glyceride biosynthesis. The evidence that the natural compound (1a) loses activity due to double bond oxidation as discussed in reference (v) above also means that it is of interest to synthesize the tetrahydro-derivative (1b) to see if the absence of a double bond leads to prolonged antifungal activity.

The C2 stereochemistry of the natural antifungal (1a) is not known, and synthesis of the compound from a precursor of known chirality would assist in the elucidation of this point. Taking all these factors into account, we required a general synthesis of the compounds (1), where both the group R and the C2 chirality could be varied at will.

THE SYNTHESIS

An obvious synthetic route to the general structure (1) is by attack of the Grignard (or organo-cadmium) reagent (3) onto the acid derivative (4) (Scheme 1). But the difficulties in working with β-oxygenated Grignard reagents (3) are well-established. A search of the literature based upon iodide (6a) disclosed no references where the Grignard reagent (3) had been usefully employed. Either β fragmentation to allyl alcohol and acetone occurs as discussed in Jung et al, J Am. Chem Soc. 1980 102 6304 or dimerisation to the diacetonide of hexane-1,2,5,6-tetraol prevails as discussed in Ariatti et al, J. Org Chem 1981 46 5204. We observed considerable fragmentation during attempts to make the Grignard reagent (3) either from the bromide or iodide.

Attempts to generate the anion from the dithiane (7a) generated from linoleic aldehyde, with a view to using this anion to displace the tosyl (or iodide) group in structure (6) (Scheme 2), failed when the butyl lithium required to generate the anion from (7a) also removed the diallylic proton in the fatty side chain, resulting in double bond migration with many products (g.c./m.s.) and a forest of $^1$H and $^{13}$C n.m.r. vinyl peaks.

The sequence (Scheme 3) from malic acid (9) (commercially available as both enantiomers) through known methodology (as referred to in the above Ariatti et al reference) to the ester (1) followed by anion generation with quenching, hopefully to give general structure (12), failed spectacularly when tested with acetyl chloride as a model fatty acid halide. The only product isolated, in excellent yield, was the acetate of the unsaturated hydroxy ester (13). This product (13) is again generated through a β-elimination of anion (11) to provide the allylic alkoxide, which is then quenched with acetyl chloride.

Attempts to generate the anion (14) or the dianion (15), with a view to condensation with the protected C4 unit (16) (Scheme 4), also failed for the unsaturated fatty acid due to double bond migration.

The reaction of the anion from dithiane (7c) with the iodide (6a) has been reported by others as discussed in De Brander et al Tetrahedron Lett. 1991 32 2821 to provide compound (8c)., (Scheme 2). However in our hands the reaction resulted only in the formation of the undesired products, the bisdithiane (18) and the alcohol (19). We postulate the first step to be attack of the dithiane anion on the iodine atom with simultaneous β-cleavage, rather than the desired displacement of iodide. The initial product (20) then reacts with further dithiane anion from (7c) to yield compound (18), while the acetone simultaneously formed by the β-cleavage of iodide (6a) reacts with further anion from (7c) to yield compound (19).

Attempts to couple the Grignard reagent (21, R=saturated) with the known aldehyde which is discussed in Saito et al Chem Lett 1984 1389 and Hanessian et al., J. Chem. 1987 65 195 (22) (Scheme 5) were not explored, exhaustively,-, but provide none of the desired coupled product (23). Rather, yields of dimer (24) and monomer (25) despite the apparently anhydrous and aprotic conditions) were obtained.

The successful synthetic route is presented in Scheme 6. The dithiane (8c), available through the aldehyde (22) from either malic acid (9) or butane-1,2,4-triol, and therefore available as either enantiomer, has been described in the literature in the Saito et al. reference and Mori et al. Tetrahedron 1979 35 933. Compounds (8c) could be deprotonated with butyl lithium and potassium t-butoxide in tetrahydrofuran at −40°. The anion was then quenched with the appropriate fatty halide to yield the series (26). Deprotection of the acetonide gave the series (27). Various attempts at monoacetylation of the saturated compound (27b) gave variable results until it was found that transesterification with vinyl acetate in the presence of *Candida cyclindraces* lipase as discussed in Herradon et al. Tetrahedron Asymmetry 1993 4 845 cleanly generated the monoacetate (28b), and this methodology was subsequently employed with other series (27) compounds. Because of anticipated difficulties in the monoacetylation procedure (27)→(28), when it was expected that over-acylation to give the diacetate would mean that the starting diol would then need to be recovered by hydrolysis in order to be recycled, all these reactions were carried out on the dithiane-protected ketone. In the event, these fears were groundless once lipase-catalysed transesterification was employed in the step (27)→(28). The dithiane was removed with bis (trifluoroacetoxy)iodobenzene as discussed in Stork et al., Tetrahedron Lett. 1989 30 387 to provide the required keto alcohol (1). In those runs where the dithiane was removed from diol structure (27) before acetylation of the primary hydroxyl, the carbonyl deprotection proved messy, probably due to participation of the primary hydroxyl, and so the sequence as listed in Scheme 6 provides the preferred order of protection/deprotection steps.

This sequence was initially carried through in the racemic series (from racemic malic acid) with the saturated side chain, to provide a product (1b) which had spectral properties consistent with those described in the literature in the above Chang et al., reference for the tetrahydro derivative of the natural antifungal (1a). During the lipase monoacetylation in this sequence a better than 95% yield of monoacetate was obtained, indicating that while the lipase was regioselective it was not enantioselective, and our synthetic product (1b) remained racemic.

The sequence was then repeated with the doubly-unsaturated side chain to provide racemic antifungal, spectroscopically identical with the natural product (1a). Finally the sequence was performed on the enantiomer from (S)-malic acid (9), by using the iodide (32b) from linoleic acid (29), to give the (S)-enantiomer (1a). This material had an opposite sign of optical rotation to that reported in the Chang et al., reference for the natural product, which is therefore the (R)-enantiomer.

For this methodology to work in the doubly unsaturated series it was necessary to convert linoleic acid (29), through the protected tetrabromide (30) by a Hunsdieker reaction into the pentabromide (31). Deprotection then generated the unsaturated C17 bromide (32a). This sequence (Scheme 7) is a modification of the literature method as discussed in Howton et al., J. Am. Chem Soc. (1954) 78 4970. For optimum yields in the condensation step (8c)→(26a), which was the most difficult step in the synthesis, it proved advantageously to employ the iodide (32b) rather than the bromide (32a).

EXPERIMENTAL $^1$H and $^{13}$C n.m.r. spectra were recorded in CDCl$_1$ solutions upon a Jeol GX400 spectrometer. $^{13}$C multiplicities were assigned by the DEPT pulse sequence. G.c. analyses were most effectively performed upon a BP21 capillary column with helium carrier gas and flame ionisation detection in a varian 3300 instrument. Mass spectra were recorded upon a Hewlett Packard MSD 5970 spectrometer using a g.c. inlet, with high resolution m.s. data from a Kratos MS 25 RFA spectrometer. Infrared data were measured in KBr disks for crystals, or neat for oils.

The butane-1,2,4-triols were both purchased (Aldrich, both enantiomers) and synthesized from malic acid (9) (both enantiomers) by $BH_3$-$Me_2S$ reduction as discussed in Hanessian et al. above. Protection as the acetonide, followed by pyridine chlorochromate oxidation to the aldehyde (22) was as described in the literature in Hanessian et al. above and Mori et al. above. In some oxidation runs a quantity (<8%) of the dimeric ester (33) reported by Mori et al. was also observed (m.s. ion at m/z 273=M-15).

THE DITHIANE (8c)

Aldehyde (22) (~1 gm) in dry dichloromethane (30 ml) was treated overnight with propane-1,3-dithiol (2.1 equiv.) and p-toluene sulphonic acid (catalytic, ~0.02 equiv.). The reaction was monitored (g.c./m.s.) until the starting aldehyde was consumed. Considerable loss of the acetonide group occurred, resulting in the formation of diol (34) (by g.c./m.s.). 2,2-Dimethoxypropane (excess) was added and the material stirred for a further 2 hr. Solid sodium carbonate was then added and the reaction stirred (2 hr). The material was filtered, the solvent removed under vacuum and the product was absorbed onto a small quantity of silica and flash chromatographed (silica, pentane/ether 4:1). Early fractions contained 2,2-dimethyl-1,3-dithiane (by g.c./m.s. and direct comparison with authentic material). Later fractions provided compound (8c) (yield ~85%). The compound (8c) has been reported previously in the Saito et al. above and in Fulop et al. Tetrahedron Lett. 1988 29 5427 but spectral data were not then recorded but which are now reported in Bullet et al., Aust J. Chem. 47 1661–1672.

THE CONDENSATION (8c) TO (26)

Typically the dithiane (8c) (~150 mg) in dry tetrahydrofuran (2 ml) was stirred under nitrogen at −40° (acetonitrile/dry ice bath) with potassium t-butoxide (1.1 equiv.). Butyl lithium (1.1 equiv.) was added and after 0.5 hr aliquots were removed, quenched with $D_2O$, and analysed (g.c./m.s., ratio of the 234:235 molecular ions) for the extent of anion formation. Appropriate further butyl lithium was added as necessary. The alkyl halide (32) or (35) (2 equiv; excess) was added neat, the mixture was held at −40° (2 hr) and then allowed to warm to room temperature. All the dithiane was consumed and some dimer from the halide (R—R) was observed (by g.c./m.s.). The solvent was removed under vacuum, a small amount of silica was added, and the product was chromatographed over silica (pentane, then pentane/ether 9:1) to afford the compound (26). Yields when the alkyl bromide was employed were ~40%; when the alkyl iodide was employed were about 75%. The reaction appeared to be adversely affected by the slightest trace of moisture.

The saturated compound (26b) was an oil and spectral data are referred to in Bull et al. above.

The spectral data of the unsaturated compound (26a) are also discussed in Bull et al. above.

Some samples of this unsaturated material (26a) showed trace $^1H$ n.m.r. peaks at δ 7.5, m, and 7.7, m; characteristic of a conjugated diene side chain.

REMOVAL OF THE ACETONIDE FROM DITHIANE (26)

The acetonide (26) (typically ~150 mg) was refluxed overnight in a mixture of acetic acid, tetrahydrofuran and water (~5:5:2). The solvent was removed under high vacuum, a small of silica was added, and the product was chromatographed (silica, pentane/ether 1:1 to 1:3) to afford the diol (27) in quantitative yield.

The saturated dithiane diol (27b) was an oil and spectral data are also recorded in Bull et al. above.

The unsaturated dithiane diol (27a) was an oil and spectral data are also recorded in Bull et al. above.

MONOACETYLATION OF THE DIOLS (27)

The diol (27) (100 mg) in vinyl acetate (3 ml) as both reagent and solvent was slowly stirred with *Candida cyclindracea* lipase (50 mg), following the general procedure of Herradon et. al. above who examined lipases from a number of sources. After 48 hr the mixture showed monoacetate (28) (95%) and starting material (27) (5%); with no diacetate (by t.l.c., with comparisons against authentic materials). Ether (10 ml) was added and the mixture stirred (20 min) to clump the lipase. The solution was filtered and the solvent was removed under vacuum. A small quantity of silica was added and the material was chromatographed (silica, pentane/ether 1:1) to provide, as the first major peak, the monoacetate (28) (~90% isolated yield).

The saturated dithiane monoacetate (28b) was an oil and spectral data are also recorded in Bull et al. above.

The unsaturated dithiane monoacetate (28a) was an oil and spectral data are also recorded in Bull et al. above.

REMOVAL OF THE DITHIANE FROM COMPOUNDS (28)

The dithiane (28) (100 mg) was treated with bis(trifluoroacetoxy)-iodobenzene as discussed in Stork et al. above. (1.1 mole equiv) for 5 min in a mixture of methanol and water ((2 ml, 9:1). The product was taken to dryness under high vacuum, a small amount of silica was added, and the material loaded onto a dry silica column. Elution with pentane/ether (1:1) gave the ketone (1) in near quantitative yield.

The saturated compound, racemic 2-hydroxy-4-oxo-henicos-1-yl acetate (1b) (from racemic malic acid) had m.p. 62° (from pentane/ether 4:1) had spectral data also referred to in Bull et al. above.

The unsaturated compound (2S)-2-hydroxy-4-oxo-henicosa-12Z,15Z-dien-1-yl acetate (1a) from ($)-malic acid) was an oil and spectral data of this compound are also recorded in Bull et al. above.

Racemic (1a), an oil, had identical spectral data with the unsaturated compound 1(a).

PRELIMINARY SCREENING OF THE ACTIVITY OF COMPOUNDS 1(a) AND 1(b) AGAINST HUMAN BREAST AND OVARIAN CANCER CELL LINES

INTRODUCTION

A pilot study was undertaken to investigate the potential anti-growth properties of an extract from avocado trees (persin). Our extensive experience in assaying the cytotoxicity of chemotherapeutic agents in cell lines and primary cultures of human ovarian cancer using a tritiated thymidine incorporation assay as discussed for example in Hayward et al. Int. J Cell Cloning (1922) 10 182–189.

We have also used a number of other assays with different end points as comparisons to our tritiated thymidine assay. MTT dye reduction as discussed in Mossman J Immunol Meth (1983) 65 55, LDH release as discussed in Decker et al. J Immunol Meth (1988) 15 61–69, clonogenic growth on plastic as discussed in Parsons et al. Aust. J Exp. Biol. Med Sci (1979) 57 161–170 and neutral red dye uptake as discussed in fort et al. J Clin Microbiol (1985) 21 689–693 have all been established techniques used in the laboratory.

For purposes of using a rapid, simple and cheap method of pre-screening cytotoxicity, we chose the neutral red dye uptake procedure to test such activity in the given extract.

METHODS AND MATERIALS

Human breast and ovarian cancer cell lines were maintained in RPMI 1640 culture medium supplemented with 10% fetal calf serum, 2 mm L-glutamine and penicillin, streptomycin and fungizone. Cells were passaged by trypsinization and plated in 96-well flat-bottomed tissue culture plates at $5 \times 10^4$ cells per well. Cells were preincubated for 6 hours at 37° C., 5% $CO_2$ in a humidified atmosphere to allow cell attachment prior to addition of the extract.

Persin was dissolved in DMF (supplied by National Research Centre for Environmental Toxicology) to give a stock solution of 100 μg/ml. Preliminary experiments indicated that DMF was not toxic to cells at 0.1%. 10 μl of the solution was added to quadruplicate wells in doubling dilution from 10 μg/ml to 0.3125 μg/ml (final concentration). Control wells had tissue culture diluent added only. DMF controls had DMF added to a final concentration of 0.1%. The extract was incubated with the cells for 20 hours before being gently aspirated. Cells were washed twice with Hanks Balanced Salt Solution (HBSS) with centrifugation in special microtiter plate carriers between washes so as not to lose viable but dislodged cells.

Neutral red was prepared fresh before each experiment from a 1% stock solution. One hundred microtiters of working solution (67 μg/ml in HBSS) was added to all wells and incubation continued for a further 4 hours. Non-absorbed dye was removed by washing cells as described above.

Absorbed dye was extracted from cells by adding 100 μl of 50% ethanol in 1% acetic acid.

Plates were mixed thoroughly to allow full extraction of the dye and were then read in a Multiscan plate reader at 540 nm. Dose response curves were constructed by plotting the percentage of untreated/control well OD540 versus concentration of extract. Individual extract concentration points were tested in quadruplicate and the results presented are averaged from 2 separate experiments.

RESULTS

FIG. 2 shows the dose response curves for the cell lines tested. Results should be interpreted in the context of the limited number of cell lines tested but the human breast cancer cell lines were more sensitive to the extract than the other cell lines. Notably, one human colon cancer cell line was not affected by the extract at any dose tested. The reasons for this are unknown.

CONCLUSION

The neutral red dye uptake assay was able to demonstrate differential effects of the extract (persin) against human breast, ovarian and colon cancer cell lines. Three human breast cancer cell lines showed greater sensitivity to the extract than other cell lines tested.

The tetrahydro derivative, (R)-2-Hydroxy-4-oxohenicosan-1-yl Acetate is compound 1(b) in FIG. 1 and is called for the sake of convenience RMC328.

RMC328 was synthesised as the R-enantiomer by hydrogenating avocado leaf extract. Chromatographic isolation was simple and produced pure product.

Both compounds as shown in FIGS. 2–8 have been tested using the neutral red dye uptake assay to assess in vitro cytotoxicity. Human breast (MCF7, ZR75, T47D), ovarian (CI-80-13S), colon (LS174T) and mouse mammary carcinoma (TA3-HA) cell lines were tested.

FIGS. 2–8 show the dose response curves for the six cell lines tested. Persin is repeated with RMC328 on a second occasion. The actual concentration of compound which reaches the cells is unknown.

Differential sensitivity to persin and the saturated analogue RMC328 was observed between the cell lines with the three human breast cancer cell lines showing the greatest sensitivity to the compounds.

One can speculate that the biological activity may be due to the fact that the molecule can interfere with normal lipid biosynthesis. Persin has an extremely close structural relationship to the monoglyceride of linoleic acid (compound 2(a)), down to the position and (Z,Z) stereochemistry of the two double bonds.

PATHOLOGY—METHODS AND MATERIALS

PLANT MATERIAL

Fresh leaves were picked from a mature Guatamalan type avocado tree (AQ 487321) growing in a commercial avocado nursery in northern New South Wales. The leaves were stored at −20° C. for 4 weeks before they were freeze-dried, ground to a fine powder and stored at −20° C. until used.

TOXICITY TESTING

White lactating female Quackenbush mice of body weight 40–50 g were used. All animal experiments followed the code of practice for the care and use of animals for experimental purposes as outlined by the Australian National Health and Medical Research Council. For the toxicity testing of leaf and crude extracts, on the fourth day after parturition the litter of each mouse was reduced to eight pups and weights of dam and litter respectively recorded. The dam was then separated from the litter and fasted overnight. On the following day and for 24 hours thereafter, the dam was offered 20 g of powdered commercial rodent diet containing 5% of powdered freeze-dried avocado leaf. In the case of preliminary organic extracts of the leaf, equivalent quantities were added to 20 g of powdered rodent diet, mixed thoroughly and the solvent evaporated under reduced pressure. After 24 hours on the medicated diet, regular untreated cubed diet was provided and the litter restored to the dam. At later stages of the isolation and purification of the active principle, the compound was suspended in up to 1 ml of 1% Tween 80 or Intralipid and given as a single dose by gavage on days 4 to 5 of lactation without prior fasting of the dam and simultaneous temporary removal of her pups. The dam and her pups were weighed daily. Failure of the pups to gain weight at the same rate as untreated controls together with absence of weight loss by the dam over the same period suggested an adverse effect of the treated diet on milk production. From 3 to 7 days after exposure to the avocado supplemented diet, or gavage of the purified extracts as the case may be, the dam was euthanased with carbon dioxide and all mammary glands and heart removed and fixed in buffered neutral 10% formalin for pathological examination.

INSTRUMENTATION

Optical rotations were measured on a Perkin-Elmer model 241 spectropolarimeter at 22° C. IR spectra were recorded on a Perkin-Elmer model 683 instrument. UV spectra were recorded on a Shimadzu model UV-160. $^1$H-NMR spectra and the long-range 2D heteronuclear experiment HMQC (Heteronuclear Multiple Quantum Coherence) were recorded on a Varian VXR-500 VXR-500 NMR spectrometer. $^{13}$C-NMR spectra, the 2D homonuclear experiment $^1$H—$^1$H COSY (Correlation Spectroscopy), and the 2D heteronuclear experiment HETCOR (Heteronuclear Correlation) were recorded on a Vrian VXR 300S spectrometer. The chemical shifts are reported in ppnm. Samples were run using $CDCl_3$ as the solvent with TMS or $CHCl_3$ as the internal reference (s, single; d, doublet; t, triplet; q, quarter; quin, quintet; m, multiplet; b, broad). High and low resolution EI mass spectra were obtained using a VG Micromass 7070F spectrometer operating at 70 eV. GC-MS were run on a Hewlett Packard model 5970B system.

STRUCTURE DETERMINATION

The purified persin was examined by TR, NMR, UV spectroscopy and mass spectrometry. A maxima at 3460 $cm^{-1}$ in the IR spectrum and a broad singlet at 3.24 ppm (exchangeable with $D_2O$) in the $_1$H-NMR spectrum both indicated the presence of an OH group. IR maxima at 1740 and 1720 $cm^{-1}$ together with $^{13}$C signals for two quaternary carbons at 170.8 and 210.7 ppm indicated that an ester and ketone were present. A singlet at 2.06 ppm in the $^1$H-NMR spectrum provided evidence for the presence of an acetate group, which was further supported by its EI mass spectrum which contained an ion at m/z 302 corresponding to the loss of acetic acid from the highest observed mass ion at m/z 362. NMR data showed that two disubstituted double bonds were present in a long hydrocarbon chain.

High resolution accurate mass measurement of the m/z 362 ion gave the value 362.2819 corresponding to the formula $C_{23}H_{38}O_3$ (calcd. 362.2821). Since the above spectroscopic evidence indicated the presence of at least four oxygen atoms in the molecule it was postulated that the peak at m/z 362 was due to the loss of water from the molecular ion. This was supported by the observation of an $[M+NH_4]$ ion at m/z 398 in its CI spectrum and NMR data. Evidence for this structure came from information gained from a range of NMR experiments ($^1$H, $^{13}$C, APT (attached proton test), and 2D experiments: $^1$H—$^1$H COSY, $^1$H-$^{13}$C HETCOR and long range $^1$-$^{13}$C HMQC). The $^1$H-and$^{13}$C-NMR assignments are shown in Table 1.

Ozonolysis of the active compound with oxidative workup followed by diazomethane methylation gave methyl hexanoate, identified by GC-MS comparison with authentic material. This placed one double bond at C-15/16. NMR data showed that the two double bonds were methylene bridged thus placing the other double bond at C-12/13. The sterochemistry of the double bonds were both assigned as Z based on the upfield $^{13}$C-NMR shift of the methylene carbon at position 14.

From the above data, the structure (Z,Z)-1-(acetyloxy)-2-hydroxy-12,15-heneicosadien-4-one(1) could be assigned to persin.

The optical rotation of the purified active compound ($[\alpha]D^{22}$+11.98 (c=10.0 mg/ml in $CHCl_3$) corresponded well with the value previously published ($[\alpha]D^{32}$+11.3(c=4.5 in $CHCl_3$)) (Chang et al, (1975). NMR chemical shift values detailed in the two earlier papers on persin(1) correspond well with our observed values. Extensive assignments of the $^1$H and $^{13}$C-NMR chemical shifts as given in Table 1 have not previously been reported.

In order to determine the absolute sterochemistry at C2, an enantioselective synthesis of both the R and the S isomers of (1) was carried out using (−)-chlorodiisopinocampheylborane and its (+) isomer respectively as a chiral auxiliary in the directed Aldol condensation of the aldehyde(2) and methylketone (3)-(Paterson et al (1990)). Both enantiomers of (1) were produced in >90% ee. Measurement of their optical rotations showed that the natural compound possessed the R-configuration (Schäffeler et al, 1994). A full report of the synthesis will be given elsewhere. A racemic mixture of the R and S isomers was also synthesises by an alternative method has also recently been reported (Bull & Carman, 1994).

The active principle (ZZ)-1-(acetyloxy)-2-hydroxy-2-12,15-heneicosadien-4-one (1) 83 mg, yellow oil; $[\alpha]D^{22}$+11.98 9c=10 mg/ml, $CHCl_3$. EIMS (70 eV) m/z (rel. int.) 362.2819 $[M-H_2O]^+$ (calcd for $C_{23}H_{38}O_3$,362.2821) (0.05%), 320 (0.2), 302.2610 (calcd for $C_{21}H_{14}O$, 302.2610), 273 (0.5) 259 (0.6), 245 (1.2), 231 (1.5), 217 (1.1), 149 (5.7), 95 (51.8), 81 (100). CIMS (70 eV) m/z (rel.init.) 398 $[M+NH_4]^+$ 20% 379 (9), 321 (35), 303 (55), 290 (100), 213 (58), 195 (85). UV ($CHCl_3$) $\lambda$max 296 nm; 332 (sh), 368 (sh), 401 (sh). IR (neat) $\Omega$max 3460 $cm^{-1}$ (broad,OH) 1740 (strong, C=0), 1720 (strong, C=0). $^1$H-NMR ($CDCl_3$, 500 mHz) and $^-$C-NMR ($CDCl_3$, 75.43 mHZ). See Table 1.

PURIFICATION AND ISOLATION OF THE TOXIN

Milled freeze-dried avocado leaf (200 g) was extracted with $CHCl_3$ for 18 hours in a Soxhlet apparatus and the extract evaporated to dryness under reduced pressure. The residue was purified by silica gel followed by fluorisil chromatography using n-hexane, dichloromethane (DCM) and 4% EtOAc in DCM in this order as solvents. The fractions collected were monitored by TLC and the activity of each evaluated in the lactating mouse assay. Final purification of an active principle was achieved by means of XAD-2 reverse phase chromatography using $CHCl_3$/MeOH/AcOH/$H_2O$ (5:80:1:14) as solvent and preparative HPLC using isopropyl alcohol/n-hexane as solvent. The yield of the compound termed "persin" a colourless oil was 0.9 to 1% by weight.

PATHOLOGICAL EFFECTS ON THE MAMMARY GLAND AND MYOCARDIUM

Dose-ranging studies indicated that the single oral dose of persin required to induce widespread, non-fatal injury to the lactating mammary gland of the mouse is from 60 to 100 mg/kg. The injury is characterised by interstitial oedema, congestion and haemorrhage and coagulative necrosis with desquamation of the acinar epithelial cells thereby preventing lactation [FIG. 9(a) and FIG. 9(b)].

The lesions are most severe in the more distal mammary glands and can vary in severity from complete necrosis of the secretory epithelium to necrosis only of parts of some acini. In affected lobules there appears to be no regeneration of necrotic epithelium and severly affected acini a replaced within a few days by scar and adipose tissue. More detailed accounts of the pathological changes in the mammary gland of the mouse caused by persin will be reported elsewhere.

At doses of persin above 100 mg/kg, necrosis of myocardial fibres may occur and areas of myocardial fibrosis can be observed in animals surviving for seven days (FIG. 10). Hydrothoraz and/or pulmonary oedema may be present in more severly affected animals.

ACTIVITY TESTING OF PERSIN DERIVATIVES

The R and S isomers of persin were tested for activity required to induce widespread lactating mammary gland necrosis at the dose rate of 50–100 mg/kg body weight. The R isomer was active but the S isomer was inactive even as a high single dose (200 mg/kg). A mixture of isomers in equal proportions was less active than the R isomer.

The two isomers of the oleic acid derivative of persin and a mixture of these isomers when tested showed a similar response. Also the isomer of the fully reduced persin was active. Some preliminary studies indicate that the ester group is essential for activity.

The present studies have indicated that persin causes damage both to the lactating mammary gland and the heart muscle and in this respect persin seems likely to be the most significant toxic component in the avocado leaves.

Plants and compounds derived from them which are known to affect the lactating mammary gland are reviewed by Craigmill et al. (1989) and include ergoline alkaloids, *Jasminium pubescens,* colchicine and vinca alkaloids. The former two agents act to enhance the rate of normal involution of the lactogenic acinar tissue by inhibiting prolactin secretion by the pituitary gland. The latter alkaloids are microtubule inhibitors and when locally applied to the secretary acinar cells prevent ejection of milk from the cells into the acinar lumen. In neither process of inhibition of milk secretion is there coagulative necrosis of the acinar epithelium. The effect of persin and related analogues in causing inhibition of milk secretion through such a necrogenic action on the secretory epithelium appears to be unique. The mechanism of the toxic action of this compound both in the mammary gland and the myocardium remains to be elucidated. The work we have done has shown so far that the neurogenic effect on the mammary gland follows oral dosing of the compound. Insofar as the biological activity of this molecule is concerned, the R configuration of the assymetric centre is critical for activity but the degree of unsaturation of the carbon chain is not.

From a pathological point of view, the compounds of formula 1 arecytotoxic and thus function as an anti tumour agent because tumour cells grow faster than normal cells of the mammary gland and thus the compounds of formula 1 will preferentially be more toxic to tumour cells rather than to normal cells which may be regenerated.

It will also be appreciated from the foregoing that the anti-cancer or anti-lactation compound of the invention will preferably comprise 5–30 mg per ml of solvent. More suitably this will be 10–20 mg per ml of solvent. In this context the solvent will be the organic solvents described previously or the surfactant dissolved in water as previously described.

TABLE 1

Figure 1:
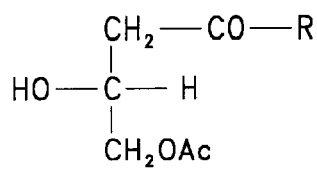
FIG. 1 and FIG. 1A show compounds.
Figure 1:
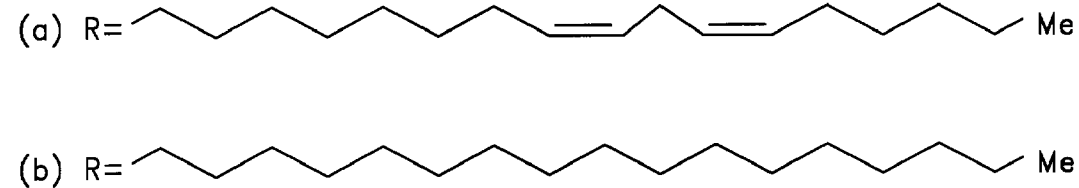
Figure 1A:
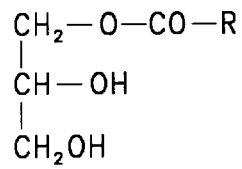
Figure 2:
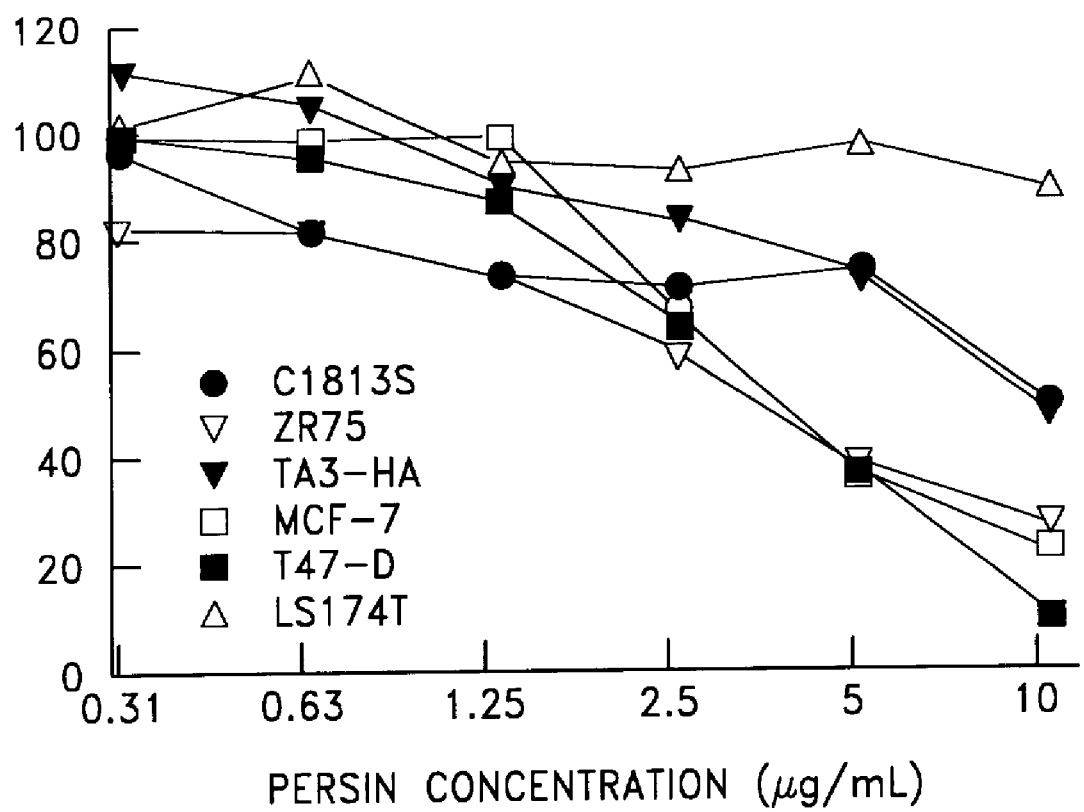
FIG. 2 Demonstration of the cytotoxicity of persin in six cancer cell lines. These cell lines were derived from human breast cancer (ZR75, MCF-7, T47-D), human ovarian cancer (CI-80-13S), human colon cancer (LS174T), and a mouse mammary carcinoma (TA3-HA). Results depict the mean percentage of control untake of the dye Neutral Red (assay of cell viability) in two separate experiments.
Figure 3:
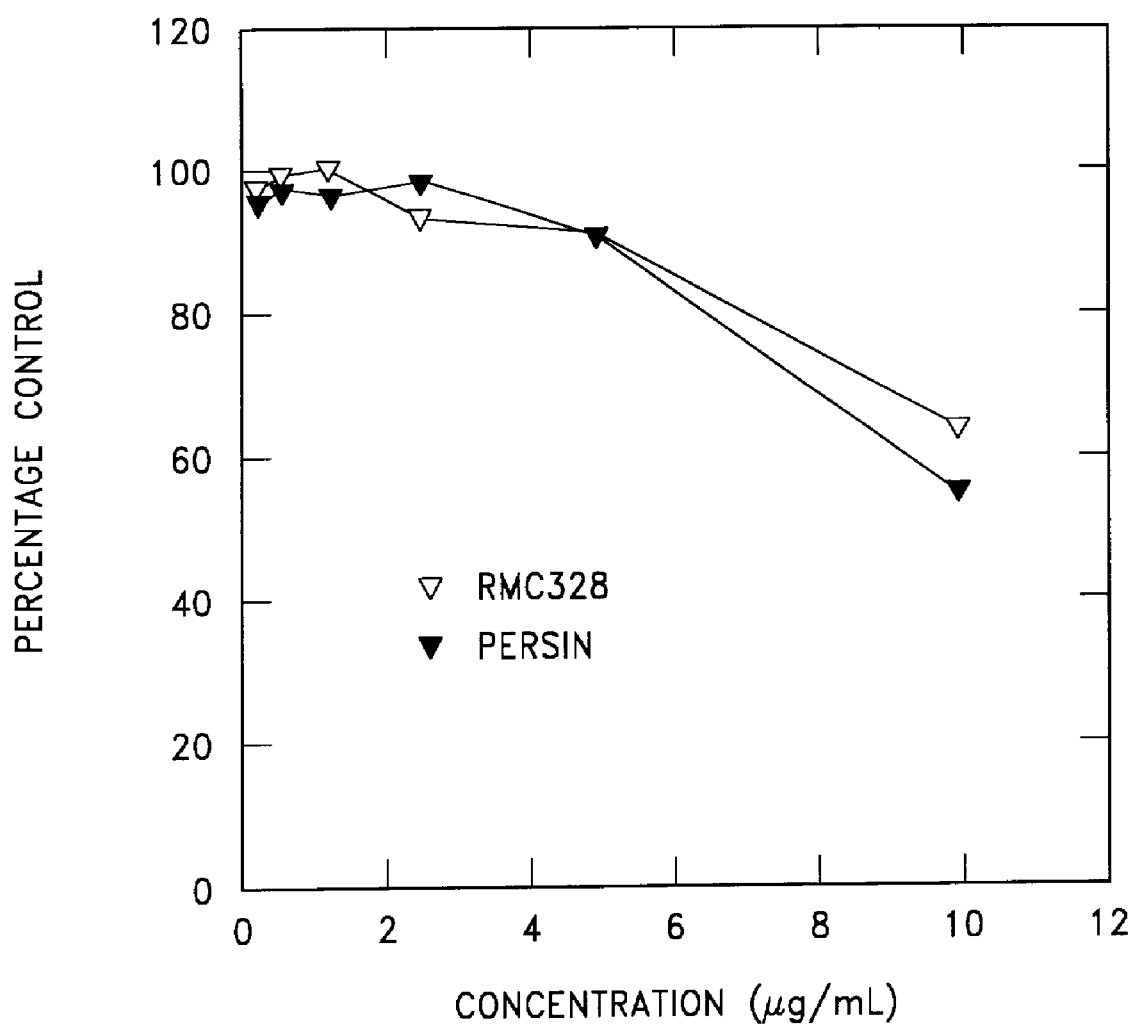
FIG. 3 Neutral Red viability assay. Human colon cancer cell line. (LS174T).
Figure 4:
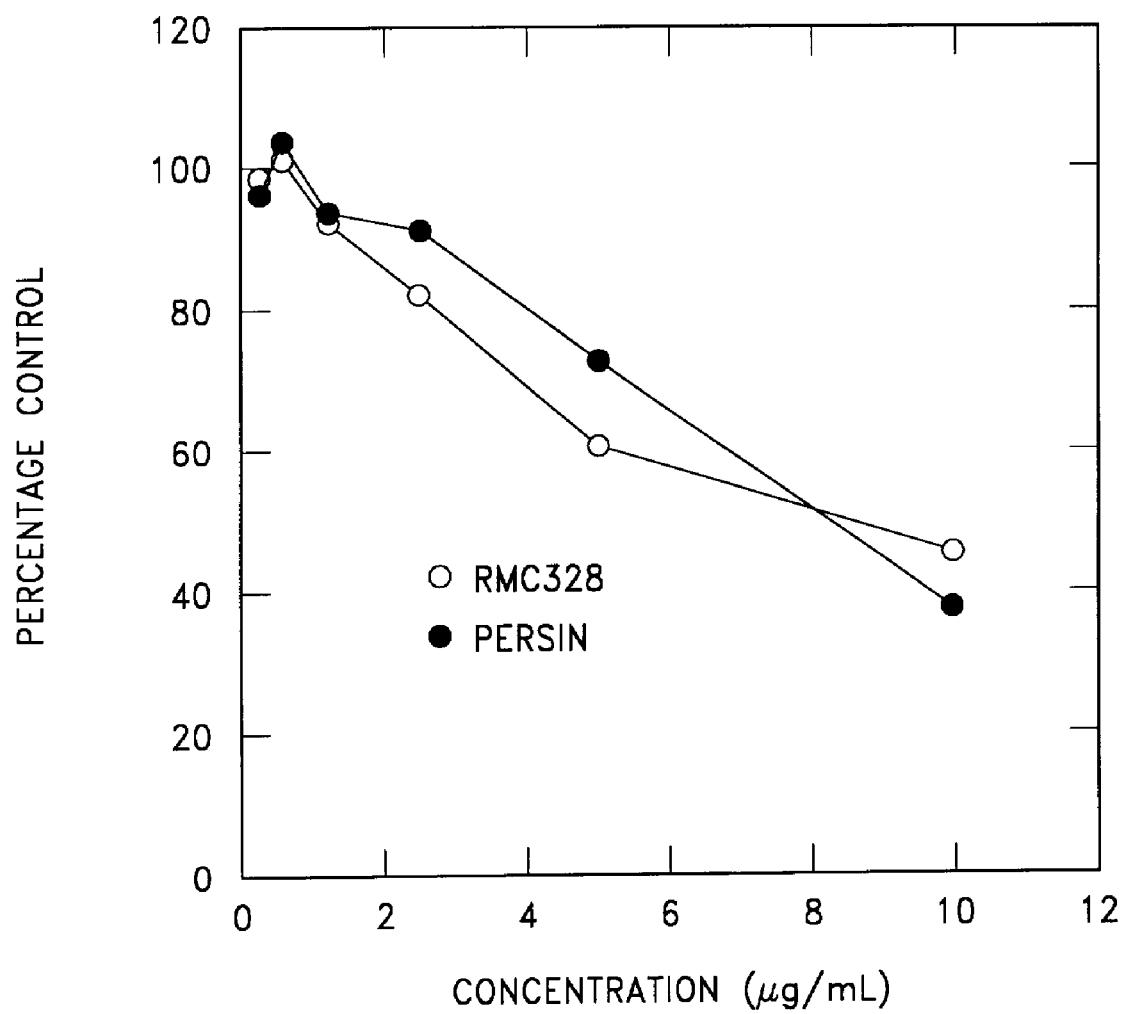
FIG. 4 Neutral Red viability assay. Human breast cancer cell line. (MCF-7).
Figure 5:
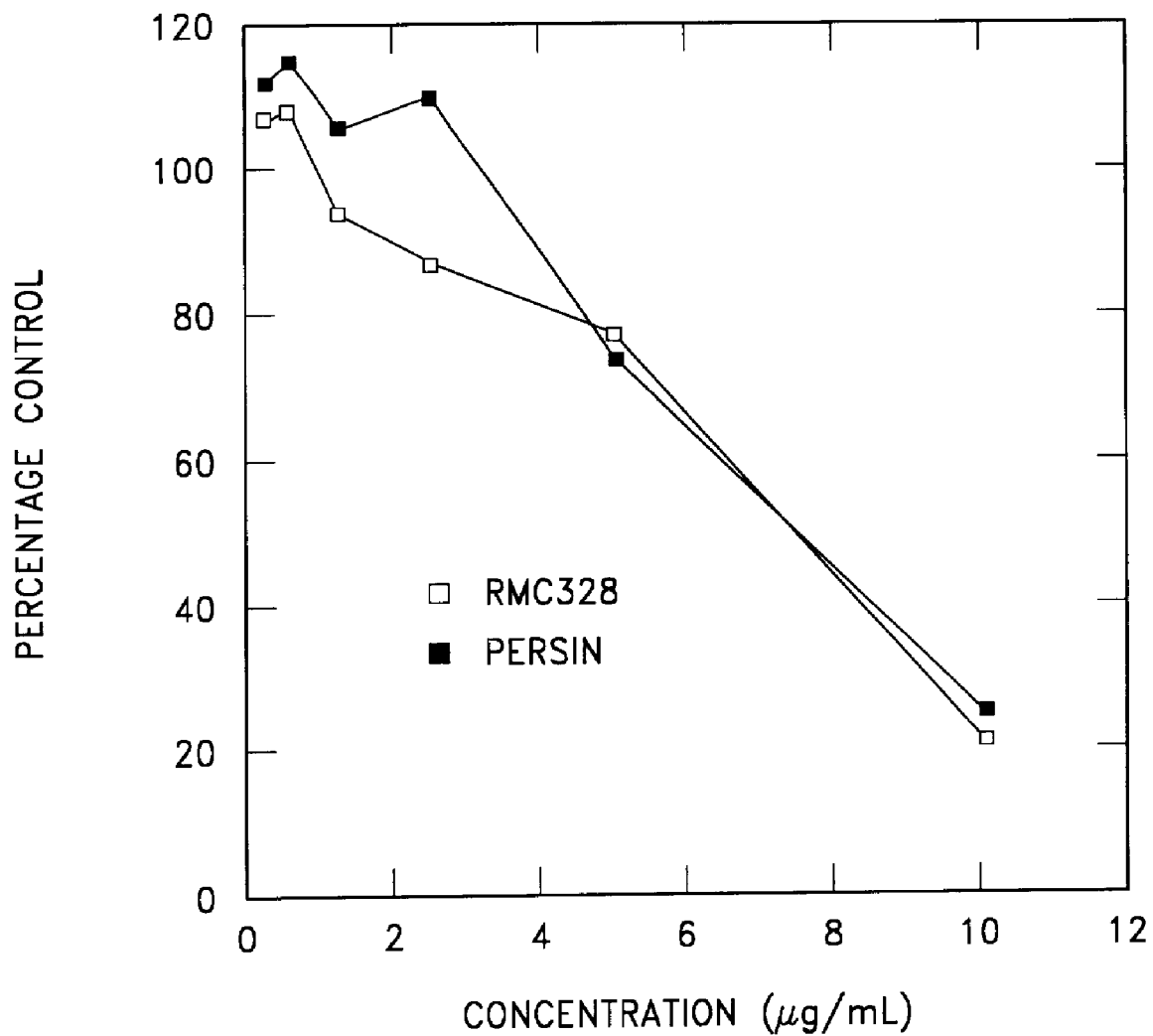
FIG. 5 Neutral Red viability assay Human ovarian cancer cell line (CI-80-13S).
Figure 6:
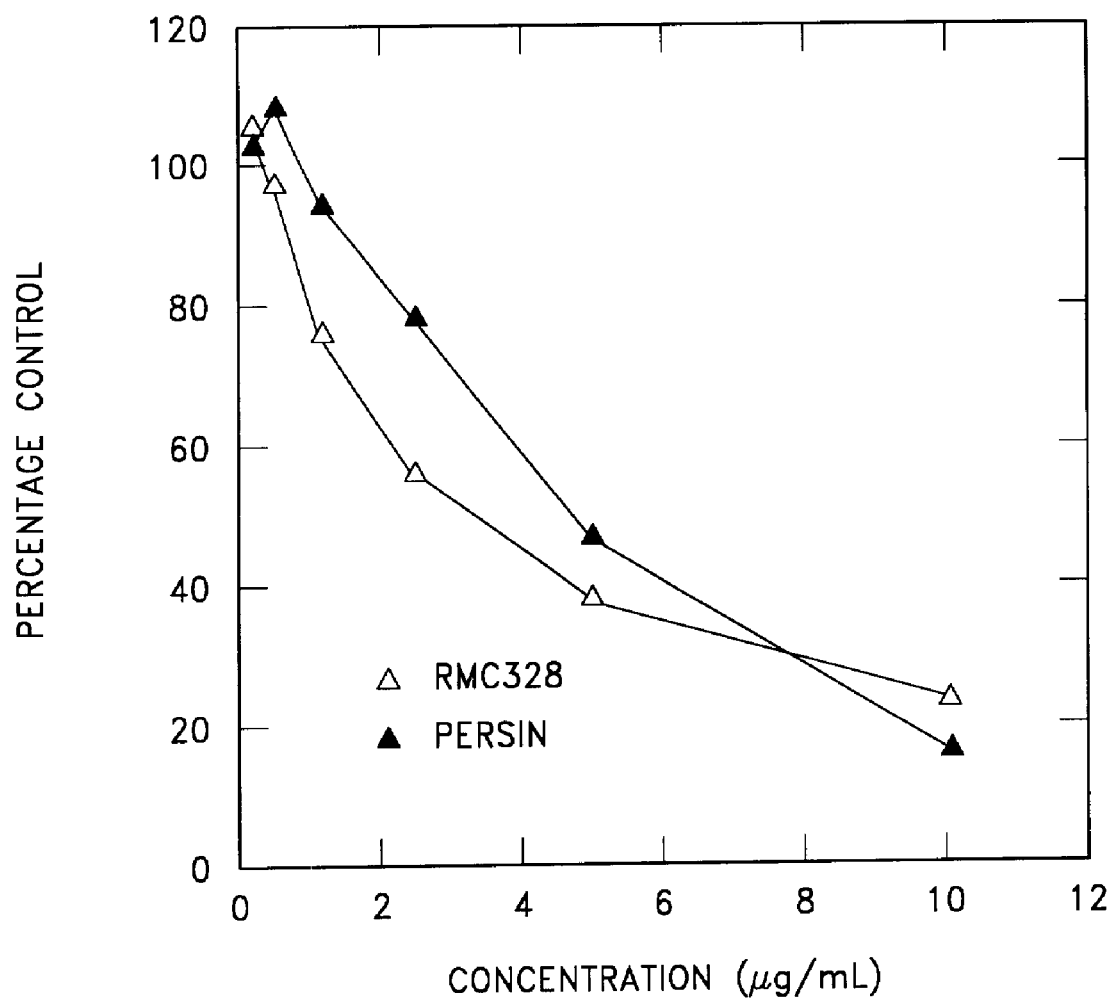
FIG. 6 Neutral Red viability assay. Human breast cancer cell line. (T47-D).
Figure 7:
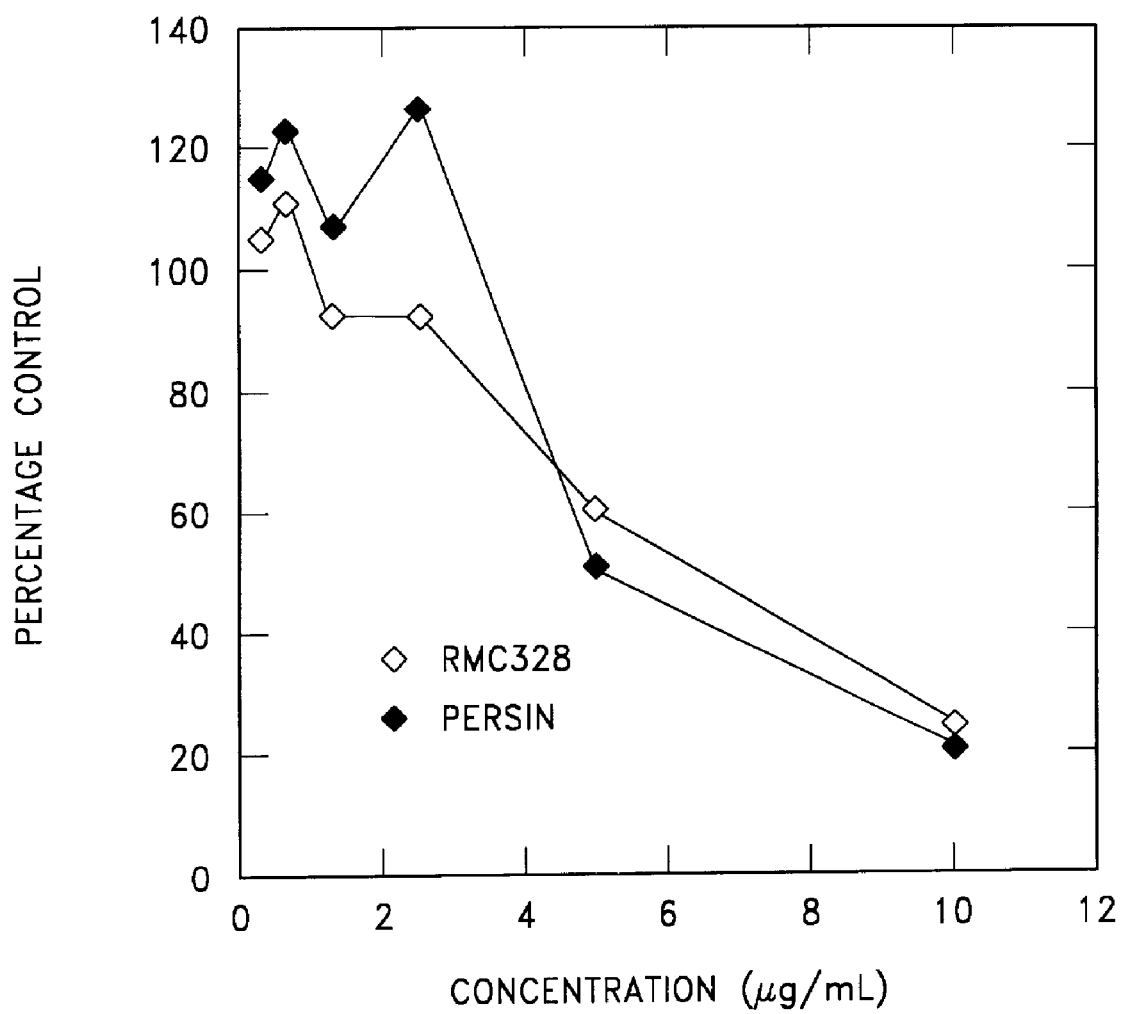
FIG. 7 Neutral Red viability assay. Mouse mammary carcinoma. (TA3-HA).
Figure 8:
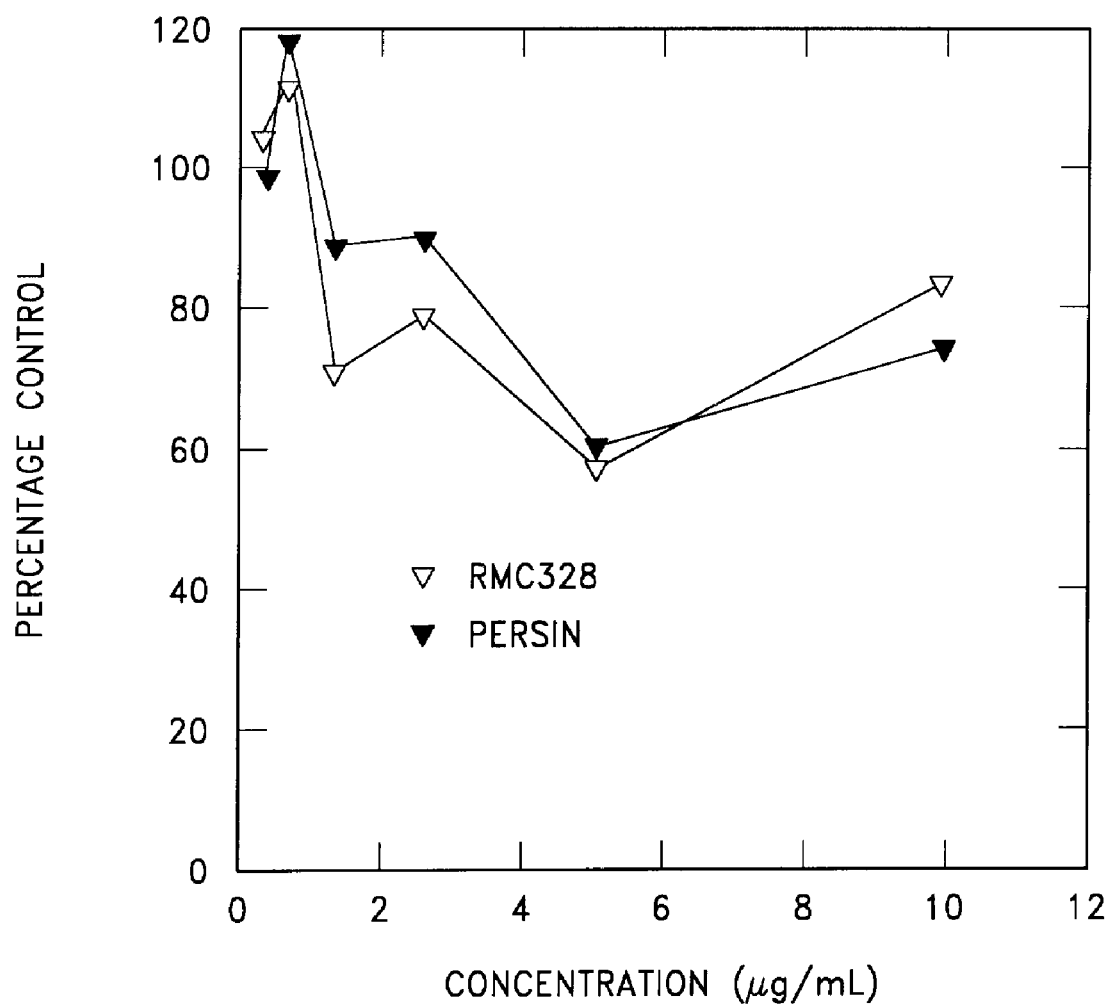
FIG. 8 Neutral Red viability assay. Human breast cancer cell line. (ZR75).
Figure 9A:
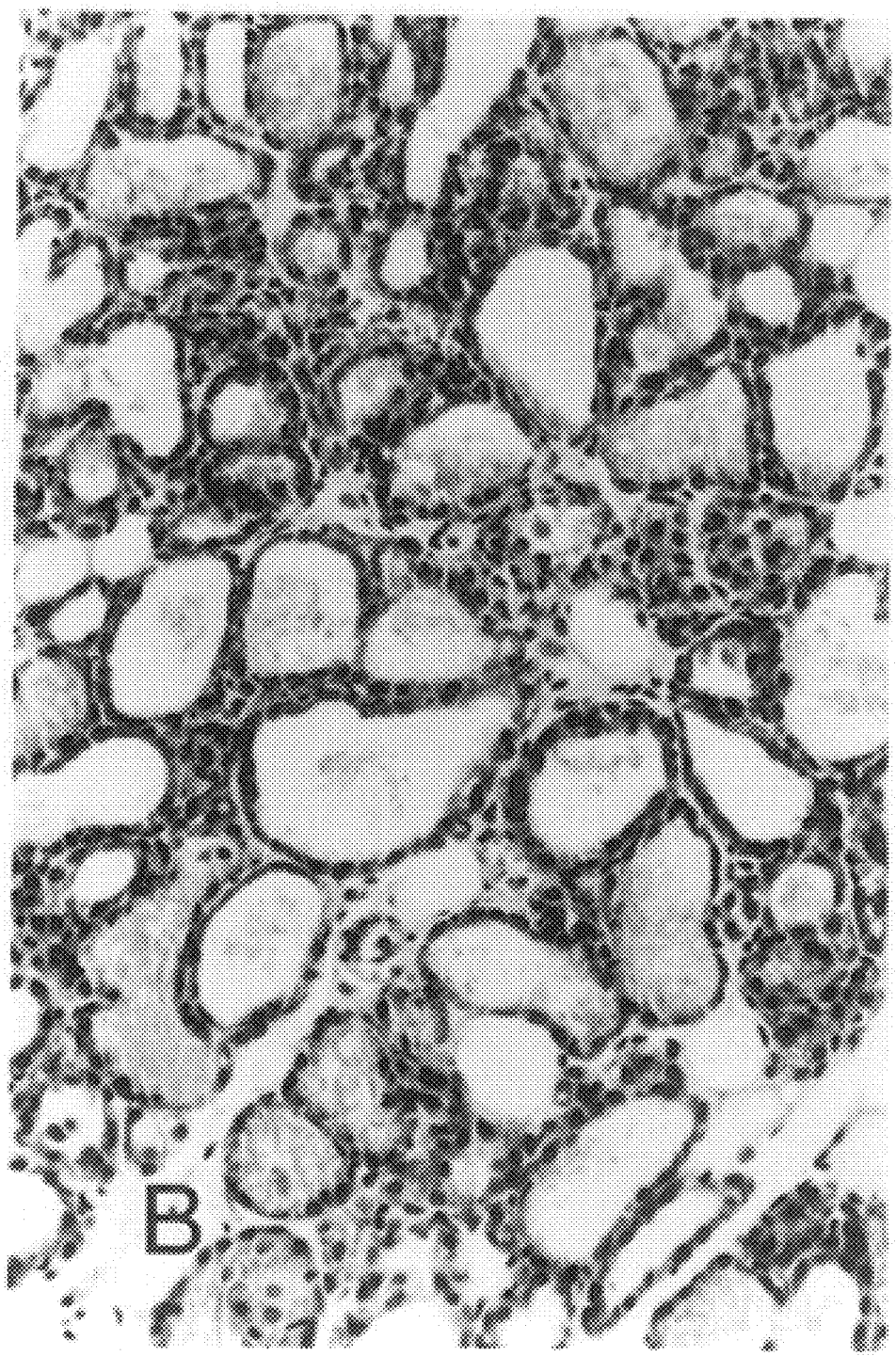
FIGS. 9A and 9B slow mouse mammary epithelium 72 hours after a single oral dose of persin at 60 mg/kg given on the 4th day of lactation. There is extensive coagulative necrosis of the secretory tissues 9A. 9B is a normal mouse lactating mammary tissue at the same stage of lactation for comparison with 9A. H&Ex250.
Figure 9B:
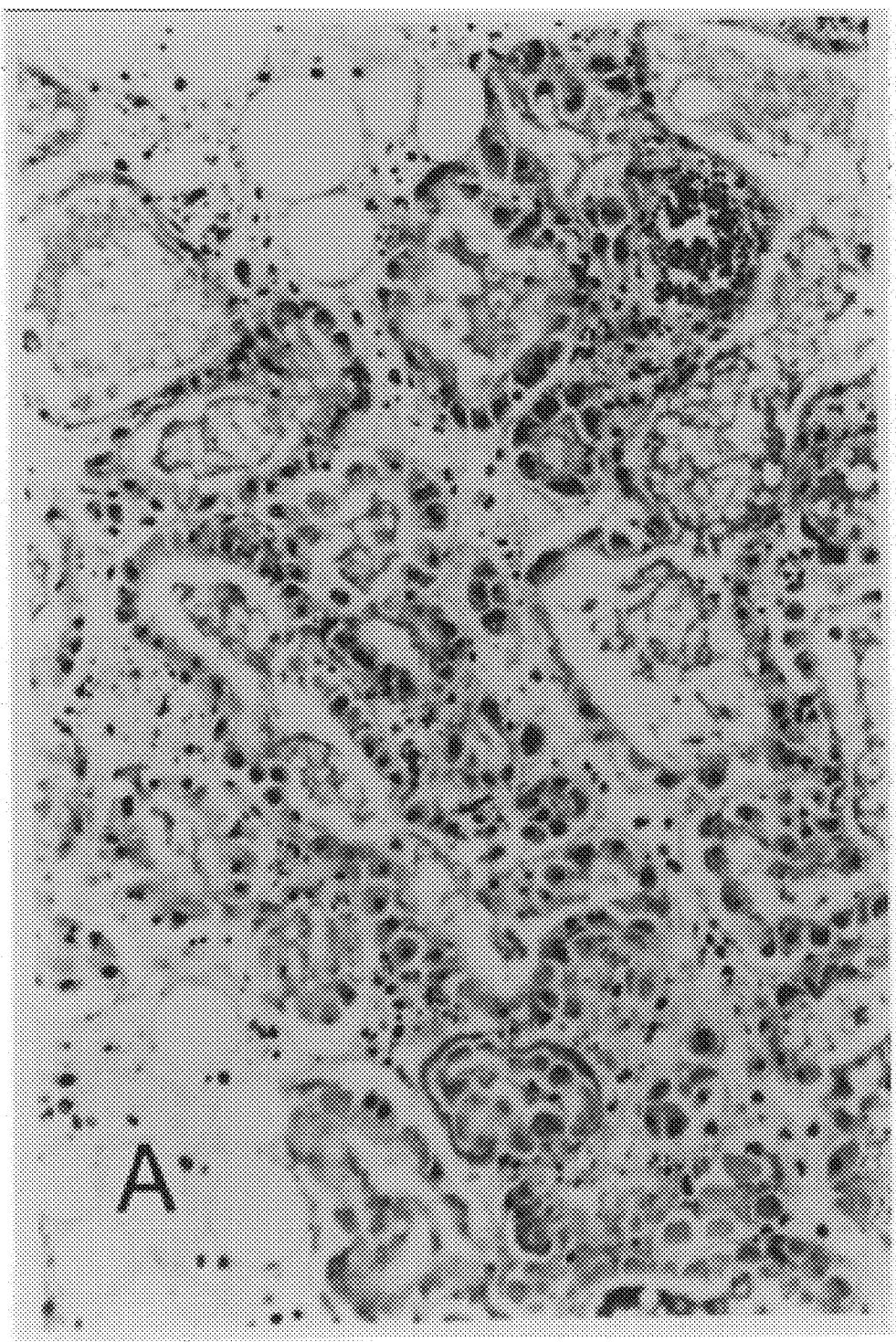
Figure 9C:
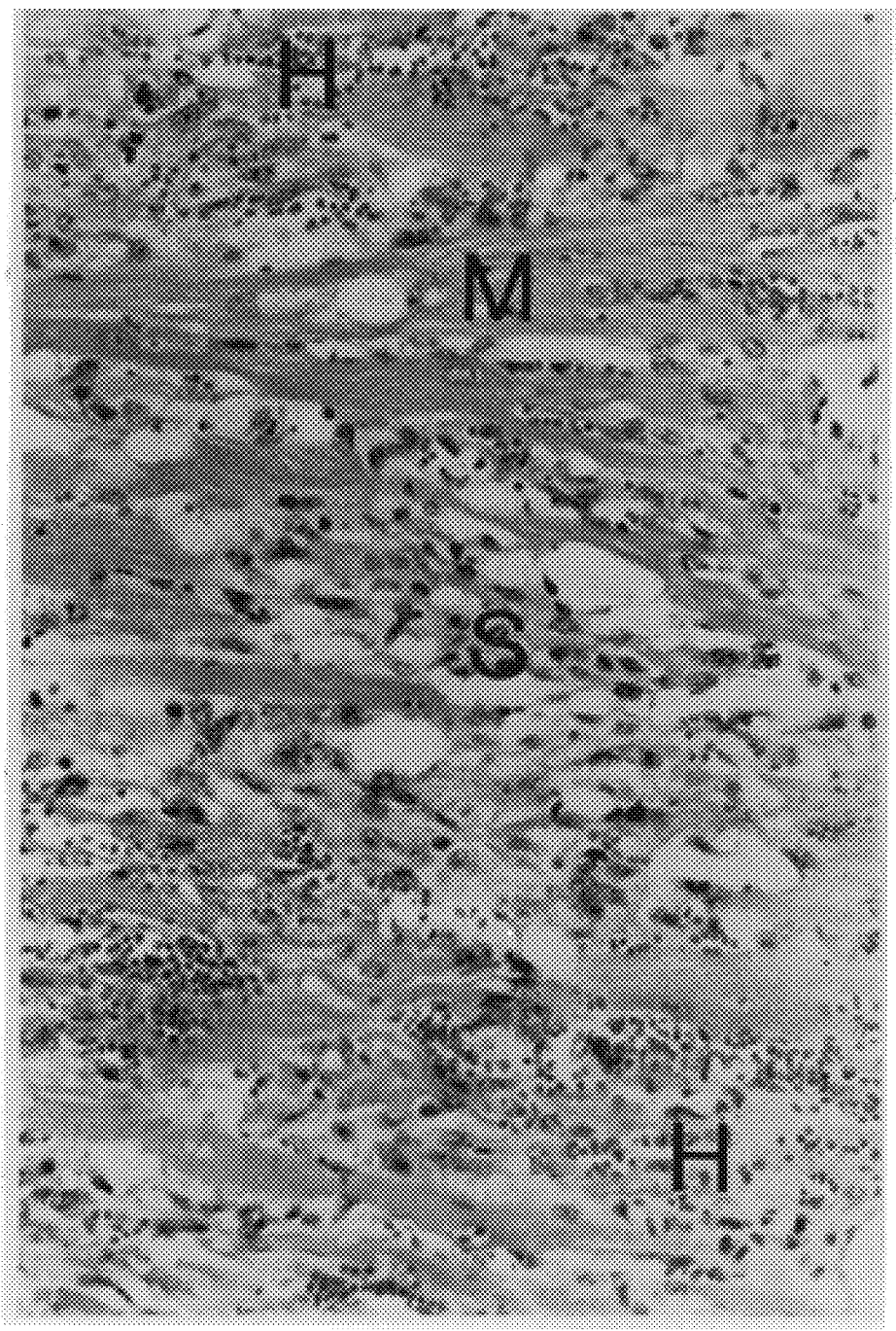
FIG. 9C This figure shows the myocardium of a house dosed orally with 100 mg/kg of persin seven days previously showing marked atrophy of muscle fibres (M) interstitial haemorrhage (H) and early scar tissue formation (S) H&EX250.

| Position | Assignment Proton | Carbon |
|---|---|---|
| 1 | 4.07 dd, J = 11.5, 4.2 | 67.1 |
|   | 4.02 dd, J = 11.5, 6.2 | — |
| 2 | 4.27 m | 65.8 |
| 3 | 2.58 dd, J = 7.5, 4.2 | 45.0 |
| 4 | — | 210.7 |
| 5 | 2.41 t, J = 7.3 | 43.5 |
| 6 | 1.54 quin, J = 7.3 | 23.4 |
| 7 | 1.26 m | 28.9 |
| 8 | 1.26 m | 29.4[b] |
| 9 | 1.26 m | 29.2[b] |
| 10 | 1.26 m | 29.1[b] |
| 11 | 2.01 dd, J = 7.3, 7.0 | 27.0 |
| 12 | 5.32 m | 130.0[c] |
| 13 | 5.32 m | 127.9[d] |
| 14 | 2.73 t, J = 6.6 | 25.4 |
| 15 | 5.32 m | 127.7[d] |
| 16 | 5.32 m | 129.8[c] |
| 17 | 2.01 dd, J = 7.3, 7.0 | 27.0 |
| 18 | 1.26 m | 28.9[b] |
| 19 | 1.26 m | 31.3 |
| 20 | 1.26 m | 22.4 |
| 21 | 0.85 t, J = 6.9 | 13.9 |
| $CH_3CO_2$ | — | 170.8 |
| $CH_3CO_2$ | 2.06 s | 20.6 |
| OH | 3.24 bs | — |

TABLE LEGENDS
TABLE 1
[1]—H— and $^{13}$C-NMR Data for Compound (1)[a]
[a]Solvent $CDCl_3$; chemical shifts in ppm from TMS or $CHCl_3$; J values in Hz.
[b,c,d]Values are interchangeable.

SCHEME 7

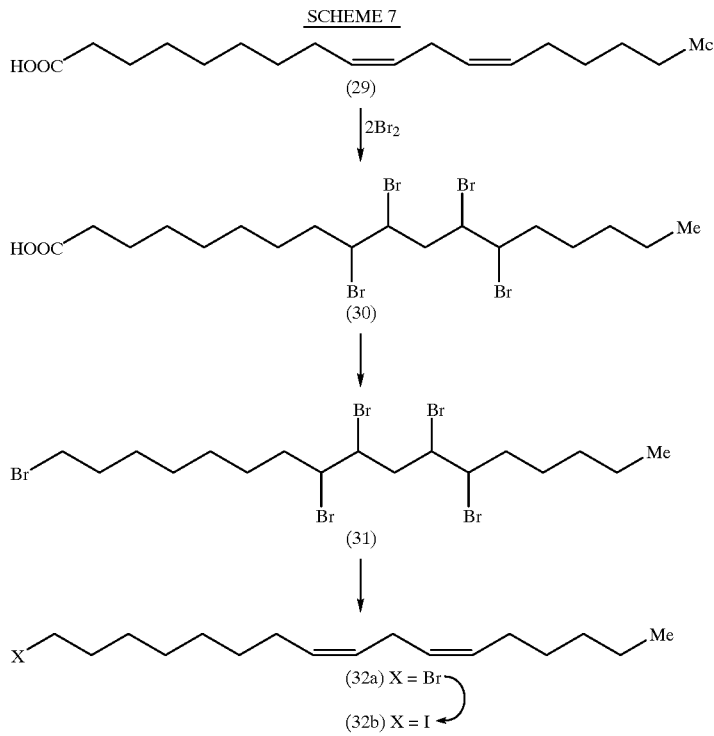

What is claimed is:

1. A method of treatment of breast or ovarian cancer of a mammal comprising administering an effective amount of a compound of formula 1 exclusive of S isomers thereof:

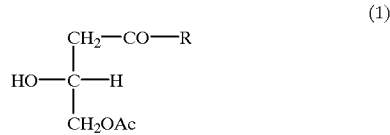

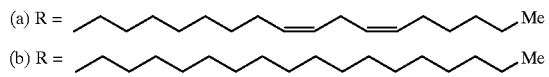

2. A method as claimed in claim 1 wherein R is of formula 1(a).

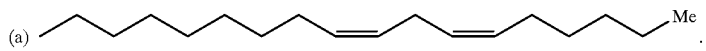

3. A method as claimed in claim 1 wherein R is of formula 1(b).

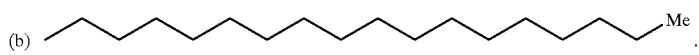

4. A method as claimed in claim 1 wherein the compound is administered up to 100 mg/kg of body weight of mammal being treated.

5. A method of claimed in claim 4 wherein the compound is administered up to 60 mg/kg of body weight of mammal being treated.

6. A method as claimed in claim 1 wherein the compound is administered orally.

7. A method as claimed in claim 6 wherein the compound is administered on a number of consecutive days at a concentration of 20–40 mg/kg of body weight of mammal being treated.

8. A method as claimed in claim 1 wherein the compound is administered utilising a composition of the compound together with a pharmaceutically acceptable non-toxic vehicle.

9. A method as claimed in claim 8 wherein the vehicle is a non-toxic surfactant or detergent which may be dissolved in water in relatively low concentrations.

10. A method as claimed in claim 9 wherein the surfactant is a non-ionic solvent which includes polyoxyethylene surfactants.

11. A method as claimed in claim 9 wherein the surfactant is selected from ethoxylates, carboxylic amides, carboxylic amides, carboxylic acid esters or polyalkylene oxide block copolymers.

12. A method as claimed in claim 8 wherein the vehicle is a non-toxic organic solvent.

13. A method as claimed in claim 12 wherein the organic solvent is selected from ethyl alcohol, propylene glycol or mixtures of ethyl alcohol and propylene glycol, dimethyl sulphoxide, dimethyl formamide or oil emulsions.

14. A method as claimed in claim 8 wherein the amount of concentration of surfactant is 0.5–10% by weight.

15. A method as claimed in claim 14 wherein the amount of concentration of surfactant is 0.5–1% by weight.

16. A method as claimed in claim 1 wherein the cancer is breast cancer.

17. A method as claimed in claim 1 wherein the cancer is ovarian cancer.

* * * * *